(12) United States Patent
Thede

(10) Patent No.: US 6,524,240 B1
(45) Date of Patent: Feb. 25, 2003

(54) DOCKING STATION FOR PORTABLE MEDICAL DEVICES

(75) Inventor: Roger C. Thede, Afton, MN (US)

(73) Assignee: Medwave, Inc., Danvers, MA (US)

( * ) Notice: Subject to any disclaimer, the term of this patent is extended or adjusted under 35 U.S.C. 154(b) by 175 days.

(21) Appl. No.: 09/721,218

(22) Filed: Nov. 22, 2000

(51) Int. Cl.$^7$ .............................. A61B 5/00; A61B 5/02
(52) U.S. Cl. ...................... 600/300; 600/485; 124/920; 124/897
(58) Field of Search ................................. 600/300, 301, 600/481, 485, 486; 128/897, 920, 903, 904

(56) References Cited

U.S. PATENT DOCUMENTS

| | | | |
|---|---|---|---|
| 5,375,604 A | * 12/1994 | Kelly et al. ................. 600/483 |
| 5,450,852 A | 9/1995 | Archibald et al. |
| 5,640,964 A | 6/1997 | Archibald et al. |
| 5,642,733 A | 7/1997 | Archibald et al. |
| 5,649,542 A | 7/1997 | Archibald et al. |
| 5,687,717 A | * 11/1997 | Halpern et al. ............. 128/903 |
| 5,687,734 A | * 11/1997 | Dempsey et al. ........... 128/903 |
| 5,720,292 A | 2/1998 | Poliac |
| 5,722,414 A | 3/1998 | Archibald et al. |
| 5,738,103 A | 4/1998 | Poliac |
| 5,797,850 A | 8/1998 | Archibald et al. |
| 5,868,135 A | * 2/1999 | Kaufman et al. ............ 600/300 |
| 5,941,828 A | 8/1999 | Archibald et al. |
| 6,183,417 B1 | * 2/2001 | Geheb et al. ................ 600/301 |
| 6,190,326 B1 | * 2/2001 | McKinnon et al. ..... 128/200.24 |
| 6,221,012 B1 | * 4/2001 | Maschke et al. ............ 600/301 |
| 6,375,614 B1 | * 4/2002 | Braun et al. ................ 128/903 |
| 6,402,691 B1 | * 6/2002 | Peddicord et al. .......... 128/897 |
| 6,409,660 B1 | * 6/2002 | Sjoqvist ...................... 128/904 |

* cited by examiner

Primary Examiner—Kevin Shaver
Assistant Examiner—Navin Natnithithadha
(74) Attorney, Agent, or Firm—Kinney & Lange P.A.

(57) ABSTRACT

A storage device for storing a plurality of portable medical devices includes a plurality of bays for receiving and storing the plurality of portable medical devices. Each portable medical device includes an electrical connector. Each bay includes a first electrical connector. The first electrical connector of each bay is configured to interface with the electrical connector of one of the portable medical devices. A second electrical connector is configured to be coupled to a computer. A battery charger is coupled to at least one of the first electrical connectors of a bay for charging a battery of one of the portable medical devices. A switch is coupled to the first electrical connector of each bay and coupled to the second electrical connector for selectively coupling each bay to the computer for data transfer between the bay and the computer.

21 Claims, 9 Drawing Sheets

DOCKING STATION FOR PORTABLE MEDICAL DEVICES

CROSS-REFERENCE TO RELATED APPLICATION(S)

None.

BACKGROUND OF THE INVENTION

The present invention relates to a system and method for storage of, and interfacing with, portable medical devices. In particular, the invention relates to a docking system and method for storing, charging, and transmitting data to and from portable medical devices, including non-invasive blood pressure measurement devices.

There has been a continuing need for devices which will measure blood pressure non-invasively, with accuracy comparable to invasive methods. Medwave, Inc. the assignee of the present invention, has developed non-invasive blood pressure measurement methods and devices which are described in the following United States patents, hereby incorporated by reference: U.S. Pat. No. 5,649,542 entitled CONTINUOUS NON-INVASIVE BLOOD PRESSURE MONITORING SYSTEM; U.S. Pat. No. 5,450,852 entitled CONTINUOUS NON-INVASIVE PRESSURE MONITORING SYSTEM; U.S. Pat. No. 5,640,964 entitled WRIST MOUNTED BLOOD PRESSURE SENSOR; U.S. Pat. No. 5,720,292 entitled BEAT ONSET DETECTOR; U.S. Pat. No. 5,738,103 entitled SEGMENTED ESTIMATION METHOD; U.S. Pat. No. 5,722,414 entitled CONTINUOUS NON-INVASIVE BLOOD PRESSURE MONITORING SYSTEM; U.S. Pat. No. 5,642,733 entitled BLOOD PRESSURE SENSOR LOCATOR; U.S. Pat. No. 5,797,850 entitled METHOD AND APPARATUS FOR CALCULATING BLOOD PRESSURE OF AN ARTERY; and U.S. Pat. No. 5,941,828 entitled HAND-HELD NON-INVASIVE BLOOD PRESSURE MEASUREMENT DEVICE.

As described in these patents, blood pressure is determined by sensing pressure waveform data derived from an artery. A pressure sensing device includes a sensing chamber with a diaphragm which is positioned over the artery. A transducer coupled to the sensing chamber senses pressure within the chamber. A flexible body conformable wall is located adjacent to (and preferably surrounding) the sensing chamber. The wall is isolated from the sensing chamber and applies force to the artery while preventing pressure in a direction generally parallel to the artery from being applied to the sensing chamber. As varying pressure is applied to the artery by the sensing chamber, pressure waveforms are sensed by the transducer to produce sensed pressure waveform data. The varying pressure may be applied automatically in a predetermined pattern, or may be applied manually.

The sensed pressure waveform data is analyzed to determine waveform parameters which relate to the shape of the sensed pressure waveforms. One or more blood pressure values are derived based upon the waveform parameters. The Medwave blood pressure measurement devices include both automated devices for continually monitoring blood pressure (such as in a hospital setting) and hand-held devices which can be used by a physician or nurse, or by a patient when desired.

When multiple hand-held or portable medical devices, such as the Medwave blood pressure measurement devices, are used in a common environment, such as a hospital, it would be convenient to provide a central storage medium for holding the devices, charging the batteries of the devices, as well as communicating with the devices to obtain stored information.

The information obtained from the devices through the docking station may be used in multiple ways. The information can be used by doctors and nurses for remote patient monitoring. The information can be used for billing purposes. Charts and graphs can be generated from the information, such as blood pressure or pulse rate historical data for a patient. The information can be used for sensor management (e.g., displaying sensor usage information, sensor test information and warnings, sensor expiration information and warnings, etc.).

BRIEF SUMMARY OF THE INVENTION

The present invention is a storage device and method for storing a plurality of portable medical devices and gathering and centrally storing a set of patient data gathered from the portable medical devices. In a preferred embodiment, the storage device includes a plurality of bays for receiving and storing the plurality of portable medical devices. Each portable medical device includes an electrical connector. Each bay includes a first electrical connector. The first electrical connector of each bay is configured to interface with the electrical connector of one of the portable medical devices. A second electrical connector is configured to be coupled to a computer. A battery charger is coupled to at least one of the first electrical connectors of a bay for charging a battery of one of the portable medical devices. A switch is coupled to the first electrical connector of each bay and coupled to the second electrical connector for selectively coupling each bay to the computer for data transfer between the bay and the computer.

A preferred method according to the present invention for gathering and centrally storing a set of patient data for each one of a plurality of patients includes applying a plurality of portable medical devices to a plurality of patients to obtain the patient data. The patient data is stored in the plurality of portable medical devices. The plurality of portable medical devices are placed in a docking station coupled to a computer. The stored patient data is transmitted from each portable medical device through the docking station to the computer and stored therein.

DETAILED DESCRIPTION

Prior to describing the docking system and method of the present invention, a description is provided of a blood pressure measurement device, which is suitable for use in conjunction with the docking system.

Figure 1:
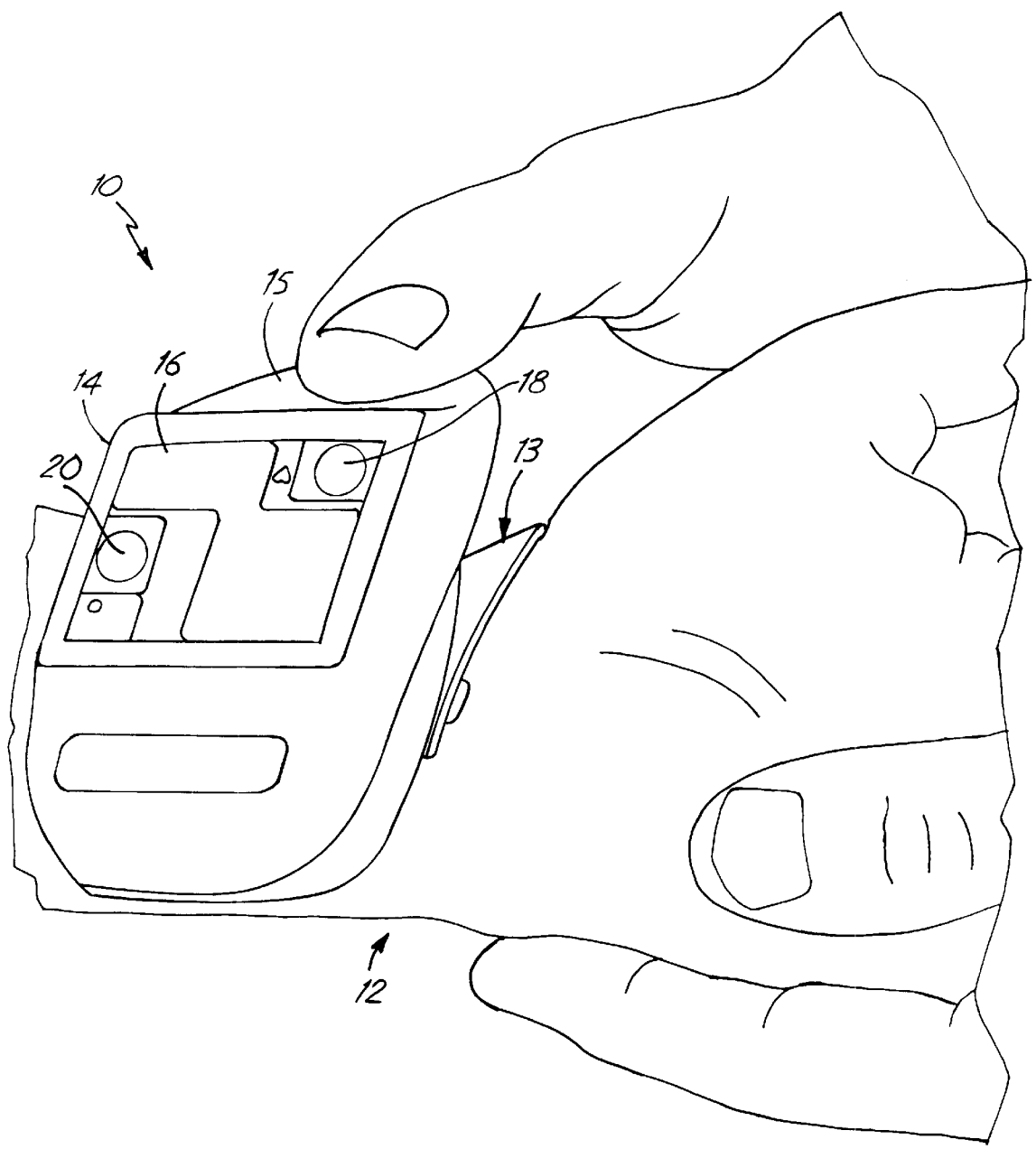
FIG. 1 is a perspective view of a non-invasive blood pressure measurement device suitable for use with the present invention.

FIG. 1 illustrates a blood pressure measurement device being used to measure and display blood pressure within an underlying artery within wrist 12 of a patient. Blood pressure measurement device 10 includes placement guide 13, main housing 14, display panel 16, patient identification toggle 18, power switch 20, and sensor interface assembly 22 (best shown in FIGS. 2A and 2B).

Using placement guide 13 of measurement device 10, measurement device 10 is placed at the projection of the styloid process bone perpendicular to wrist 12. With device 10, a small amount of force is manually applied to the radial artery, which runs along the styloid process bone. As the force is manually applied, blood pressure waveforms are recorded and the corresponding hold down pressure which is being manually applied is also recorded. Using the shape of the blood pressure waveforms, waveform parameters are generated. These parameters, along with universal coefficients, are used to calculate pressure values which then can be displayed.

Placement guide 13 is connected to housing 14 at the base of housing 14. Placement guide 13 straddles the styloid process bone, automatically placing sensor interface assembly 22 over the underlying artery. Housing 14 contains all of the electrical components of measurement device 10. The shape and configuration of housing 14 allows it to hang on the patient's wrist, using placement guide 13 as a type of hook. Housing 14 includes pressure platform 15, which is a flattened depression directly above sensor interface assembly 22. In operation, the user (medical personnel) applies pressure on pressure platform 15 with a thumb or finger. The hold-down force from the user's thumb applies a force in an axial direction (i.e., an axial direction with respect to a central cylindrical axis of sensor interface assembly 22) to wrist 12 of the patient. The axial force is transmitted from pressure platform 15 of housing 14 to sensor interface assembly 22.

In a preferred embodiment, display panel 16 simultaneously displays the following values based upon blood pressure measurements: systolic pressure, diastolic pressure, pulse rate, and mean blood pressure. Display panel 16 also preferably provides visual prompting for manually applying a varying hold down pressure.

Power switch 20 is actuated to turn on power to the circuitry within housing 14. Timing circuitry within housing 14 automatically turns power of f after a predetermined period of inactivity. Actuation of switch 20, after the unit is turned on, causes display panel 16 to indicate previous readings of blood pressure and pulse rate.

Patient identification toggle 18 is used to organize the recorded blood pressure information with respect to a particular patient. After actuating power switch 20, the user selects the specific patient for which blood pressure will be measured by pressing patient identification toggle 18. In one embodiment, display panel 16 displays a patient identification number for the currently selected patient. The patient identification number changes as patient identification toggle 18 is pressed. In one embodiment the user can scroll through a list of 16 patient identification memory locations.

Figure 2A:
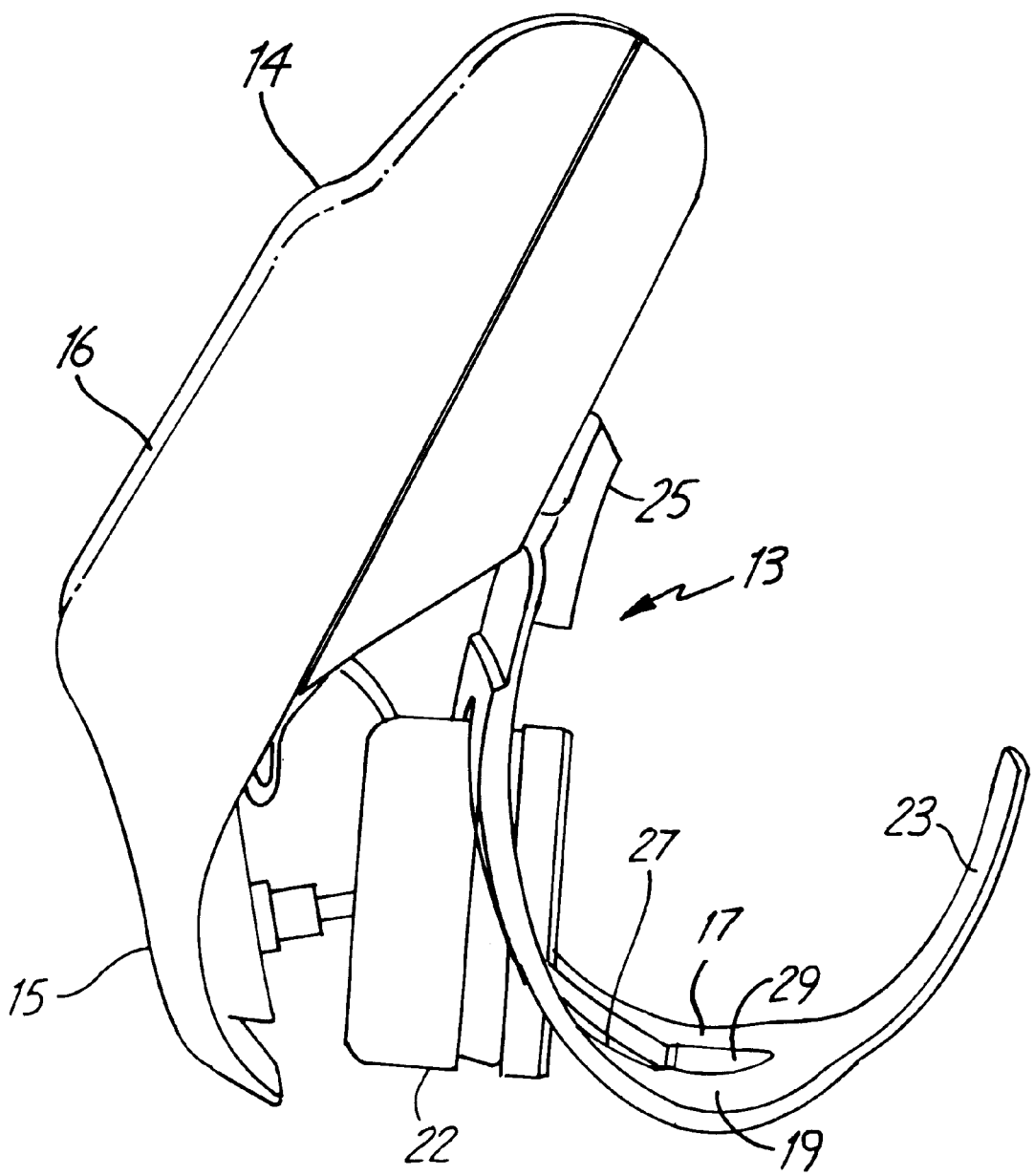
FIG. 2A is a side view of the blood pressure measurement device of FIG. 1.
Figure 2B:
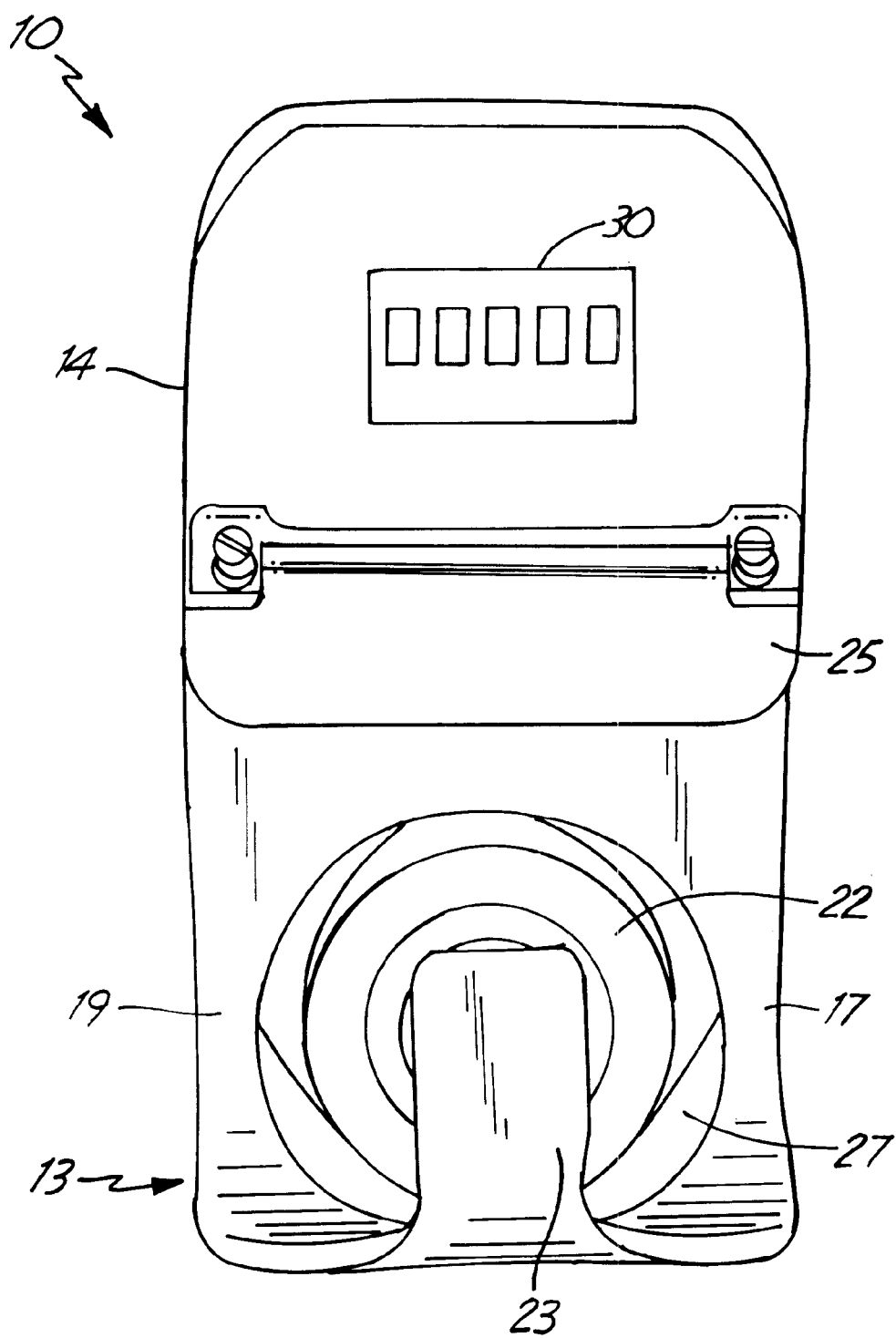
FIG. 2B is a bottom view of the blood pressure measurement device of FIG. 1.

FIG. 2A is a side view of blood pressure measurement device 10, and FIG. 2B is a bottom view of blood pressure measurement device 10. As can be seen from FIGS. 2A and 2B, placement guide 13 is generally U-shaped. Placement guide 13 includes hook 23, pad 25, and opening 27. Opening 27 is a generally circular aperture that has a notch 29 near hook 23. Guide ribs 17 and 19 encircle opening 27 and notch 29, and meet at the base of hook 23.

When device 10 is placed on the patient, pad 25 contacts the palm side of the wrist of the patient, while hook 23 wraps around the backside of the wrist. Placement guide 13 is made of a flexible plastic so as to fit all patients, with the styloid process bone fitting into notch 29 of opening 27. Opening 27 also allows sensor interface assembly 22 to come in contact with the patient's wrist. Pad 25 becomes a pivot point about which force is applied.

Relying on a cantilever type action, device 10 allows the user to apply a force at pressure platform 15 of housing 14. Housing 14 pivots about pad 25, and sensor interface assembly 22 applies an axial force to the underlying artery. Sensor interface assembly 22 is pivotally mounted to housing 14. As pressure is manually applied by moving housing 14 toward the artery, that force is transferred from housing 14 to sensor interface assembly 22.

Device 10, with placement guide 13 and the cantilever type action, allows sensor interface assembly 22 to be consistently placed in the proper position, and the hold-down force to be consistently applied in the axial direction with respect to wrist 12. This improvement greatly simplifies the procedure of applying pressure by the user, because the user no longer controls the direction and angle at which pressure is applied with respect to the patient's wrist.

Instead of having to palpate wrist 12 to identify the location of the radial artery, a user simply places device 10 adjacent wrist 12 so that placement guide 13 hooks onto the patient's wrist with guide ribs 17 and 19 straddling the projection of the styloid process bone. The measurement process is significantly simplified with the present invention.

The force applied to the artery is swept in an increasing fashion so the pressure waveform data from a series of pulses are obtained with different amounts of force being applied. To achieve the desired pattern of variable force, user feedback is preferably provided with device 10.

In a preferred embodiment, feedback is in the form of a visual counter on display panel 16. As the user begins to apply pressure, a number is displayed corresponding to the amount of pressure applied by the user. As the user increases the applied pressure, the displayed number proportionally increases. The user (medical personnel) is previously instructed to increase pressure smoothly so that the displayed counter increases one integer at a time, approximately one per second. If the user increases the hold-down pressure too quickly, the displayed counter will also jump quickly through the corresponding numbers to indicate the choppy applied pressure. The user applies greater pressure until device 10 shows the resulting blood pressure measurements on display panel 16. Preferably, the user applies enough pressure to get the counter up to the number 15, but it could be as low as 4 or 5, or as high as 27 or 28, depending on the patient. If a patient has higher blood pressure, greater applied force will be necessary, and the corresponding ending counter number will be a higher integer.

After the measurement, the user can then view the blood pressure reading. In a preferred embodiment, display panel 16 provides a digital readout of systolic, diastolic, and mean blood pressure, as well as pulse rate. An indication of memory location (by number) corresponding to the patient is also displayed.

As soon as the reading is complete, device 10 is ready to take another reading. There is no need to clear display 16. Device 10 stores a predetermined number of previous readings (such as the last 10 readings). To review prior readings, patient identification toggle 18 or power switch 20 is pressed. This causes a different reading from memory to be displayed on display 16.

Alternatively, the feedback to the user can be audible tones and/or visual movable bars. The process of applying force in response to audible tones and/or visual movable bars on display 16 is fully described in U.S. Pat. No. 5,941,828, entitled "Non-Invasive Blood Pressure Sensor With Motion Artifact Reduction", which is incorporated herein.

As can be seen in FIG. 2B, device 10 includes external connector 30. External connector 30 is a five pin connector that is used to transmit and receive data, recharge battery 36 (see FIG. 3) contained within housing 14 and provide an alternative power source to device 10. External connector 30 allows device 10 to be connected to a docking station 100 (shown in FIG. 4) so that its internal battery can be recharged, and the collected blood pressure information can be downloaded to a central system. Device 10 can be used by a nurse or other employee in a hospital setting to collect blood pressure and heart rate information from a series of patients. Docking station 100 is described below with reference to FIGS. 4–7.

Figure 3:
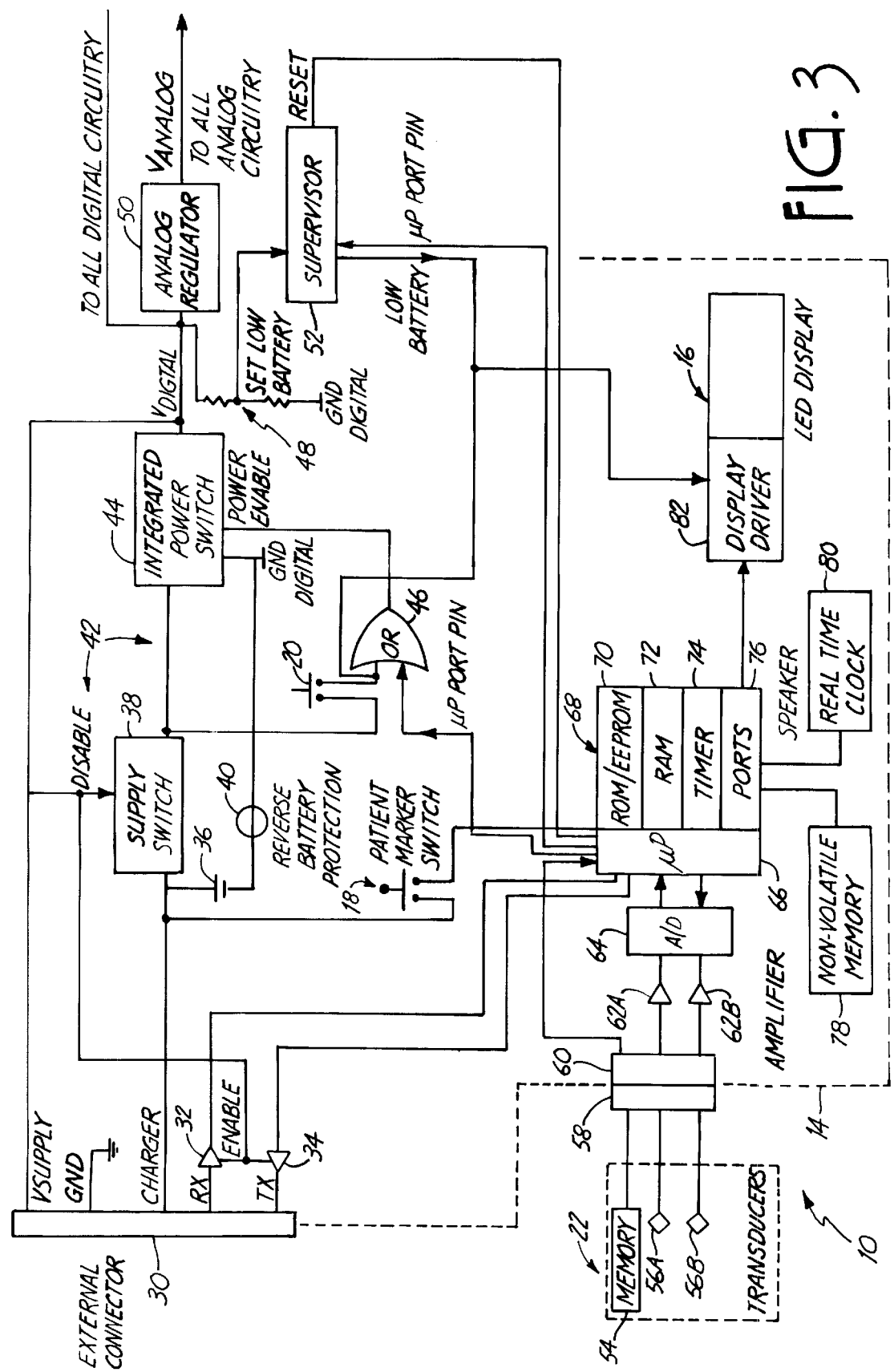
FIG. 3 is an electrical block diagram of the blood pressure measurement device.

FIG. 3 is an electrical block diagram of device 10. Device 10 includes patient marker switch 18, power supply circuit 42, sensor interface assembly 22, connectors 58 and 60, amplifiers 62A and 62B, analog-to-digital (A/D) converter 64, microprocessor 68, display driver and memory circuit 82, display panel 16, non-volatile memory 78 and real-time clock 80. Power supply circuit 42 includes external connector 30, amplifiers 32 and 34, rechargeable battery 36, supply switch 38, reverse battery protection 40, switch 20, integrated power switch 44, OR circuit 46, voltage divider 48, analog regulator 50 and supervisor circuit 52.

Device 10 can be powered through an external power source, such as docking station 100. An external power source couples to device 10 through external connector 30. Power from external connector 30 on the VSUPPLY line causes supply switch 38 to disconnect rechargeable battery 36 from supplying power to supply circuit 42. Instead, rechargeable battery 36 is recharged using the CHRGR line while the external power source supplies power to supply circuit 42 on the VSUPPLY line. External connector 30 also allows device 10 to receive and transmit data, such as blood pressure information and device serial number, to docking station 100 (see FIG. 4) over the RX (receive) line and TX (transmit) line. The RX and TX lines are coupled to amplifiers 32 and 34, respectively, which amplify the signals transmitted and received by microprocessor 68. Amplifiers 32 and 34 are enabled when power is received through the VSUPPLY line, and are disabled when no power is received through the VSUPPLY line. External connector 30 also includes a GND line, which is connected to ground.

Switch 20 is partially a monitoring pushbutton switch. Pressing switch 20 causes OR circuit 46 to turn on integrated power switch 44. Integrated power switch 44 supplies power to all digital circuits, including microprocessor 68, display panel 16 and associated display driver and memory circuit 82. Integrated power switch 44 supplies power to microprocessor 68, which in turn latches on OR circuit 46. The turn off of the circuit is controlled by microprocessor 68 discontinuing a signal to OR circuit 46. This occurs through a fixed time of no activity.

Analog regulator 50 outputs electrical power which is used to energize analog circuitry, including amplifiers 62A and 62B, and analog-to-digital (A/D) converter 64.

Pressure transducers 56A and 56B and nonvolatile memory 54 within sensor interface assembly 22 are connected through connector 58 and connector 60 to circuitry within housing 14. Transducers 56A and 56B sense pressure communicated within sensor interface assembly 22 and supply electrical signals to connector 58. In a preferred embodiment, transducers 56A and 56B are piezoresistive pressure transducers. Nonvolatile memory 54 stores offsets of transducers 56A and 56B and other information such as a sensor serial number. Nonvolatile memory 54 is, in a preferred embodiment, an EEPROM.

The outputs of transducers 56A and 56B are analog electrical signals representative of sensed pressure. These signals are amplified by amplifiers 62A and 62B and applied to inputs of A/D converter 64. The analog signals to A/D converter 64 are converted to digital data and supplied to the digital signal processing circuitry 66 of microprocessor 68.

Microprocessor 68 includes digital signal processing circuitry 66, read only memory (ROM) and electrically erasable programmable read only memory (EEPROM) 70, random access memory (RAM) 72, timer circuitry 74, and input/output ports 76. A/D converter 64 may be integrated with microprocessor 68, while some of the memory may be external to microprocessor 68.

Based upon the pressure data received, microprocessor 68 performs calculations to determine blood pressure values. As each pulse produces a cardiac waveform, microprocessor 68 determines a peak amplitude of the waveform. Microprocessor 68 controls display driver 82 to create the visual counter on display 16 that counts in correlation to the hold down pressure applied by the user. The visual counter guides the user in applying a variable force to the artery.

When a measurement cycle has been completed, microprocessor 68 reorders the cardiac waveforms in increasing order of their corresponding hold down pressure and performs calculations to determine systolic pressure, diastolic pressure, mean blood pressure, and pulse rate. The process of calculating pressure using shape, amplitude, and hold down is described in the previously mentioned Medwave patents, which are incorporated by reference. If patient identification toggle 18 is pressed, a signal is supplied to microprocessor 68, causing it to toggle to a new pressure reading with a new memory location. In one embodiment, the memory location of that pressure reading is also displayed.

The blood pressure calculations, organized by patient, are preferably time-stamped at the time of calculation using real-time clock 80, and stored in non-volatile memory 78, so that the calculations are not lost when power to device 10 is turned off. Non-volatile memory is preferably an EEPROM.

Figure 4:
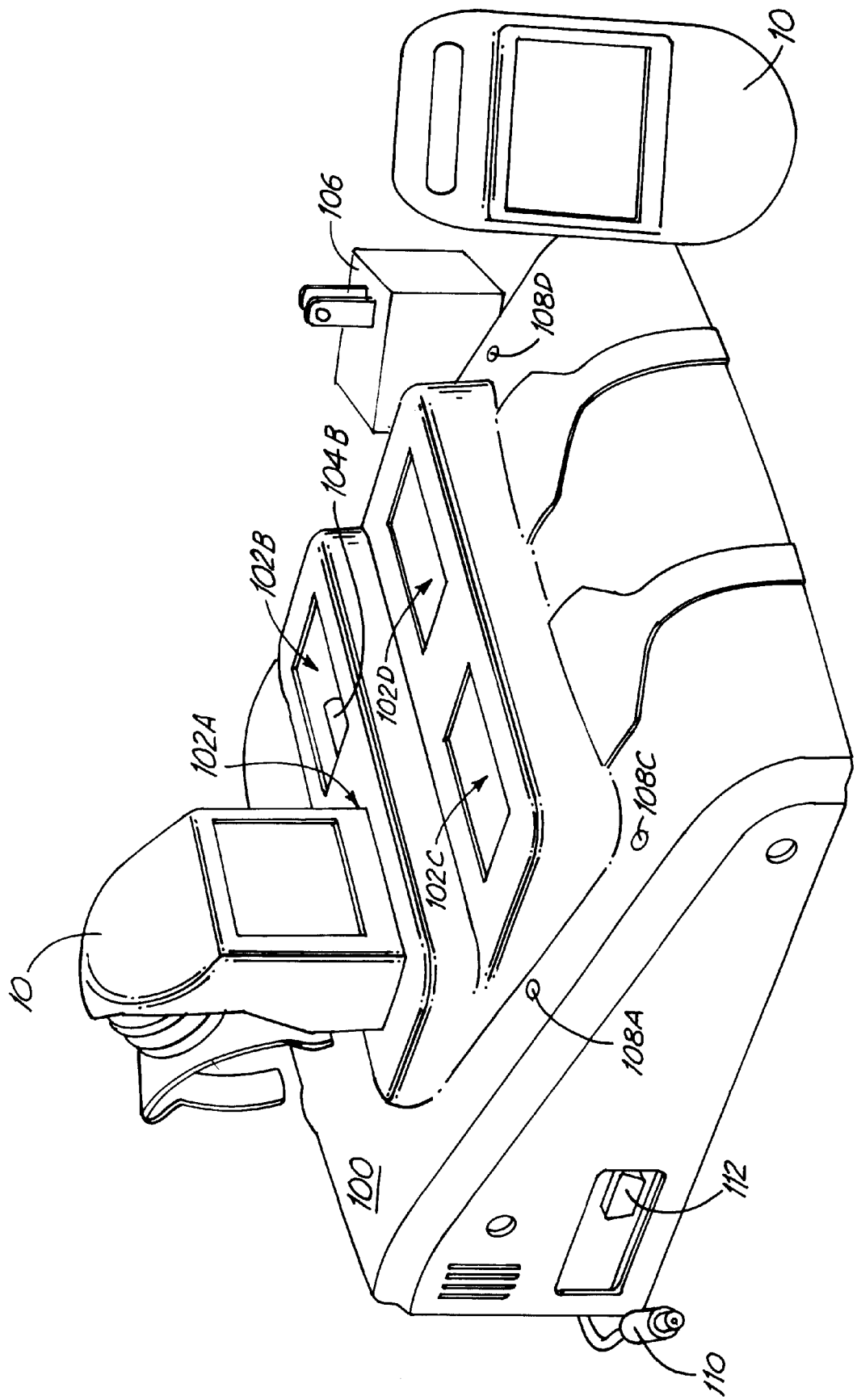
FIG. 4 is a perspective view of a docking station according to the present invention.

A preferred docking station according to the present invention is illustrated in FIG. 4. Docking station 100 includes four bays 102A–102D (collectively referred to as bays 102) for receiving and holding blood pressure devices 10. Bays 102A–102D include five-pin connectors 104A–104D, respectively, for interfacing with external connector 30 of a device 10. Only connector 104B is visible in FIG. 4, but connectors 104A, 104C and 104D are the same as connector 104B. Docking station 100 further includes AC adapter 106, LED indicators 108A–108D (collectively referred to as LED indicators 108) and DB-9 connector 112. LED indicator 108B is not visible in FIG. 4, but is positioned adjacent bay 102B similar to the positioning of LED indicator 108A adjacent bay 102A. LED indicators 108 are preferably dual color (red-green) LEDs. AC adapter 106 plugs into a wall receptacle for AC power, and outputs a DC voltage through DC connector 110. DC connector 110 plugs into docking station 100 and provides DC power for the circuitry therein. Alternatively, power for docking station 100 and for recharging devices 10 may be obtained from another source, such as from personal computer (PC) 120 (shown in FIG. 6).

Figure 5:
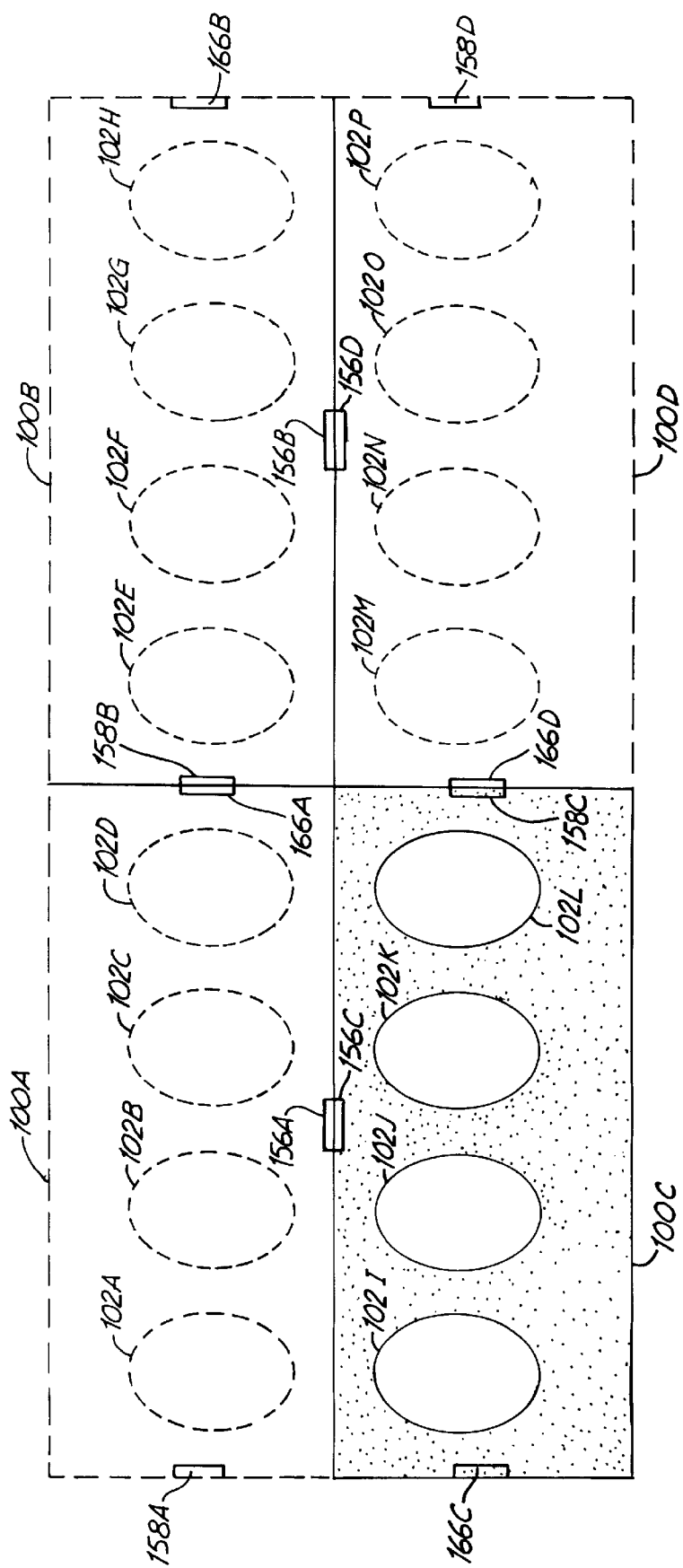
FIG. 5 is a schematic diagram of multiple docking stations coupled together.

Docking station 100 preferably has a modular design, allowing multiple docking stations 100 to be connected together. FIG. 5 shows a diagram of four docking stations 100A–100D (collectively referred to as docking stations 100) connected together. When multiple docking stations 100 are coupled together, one docking station 10A acts as a master, while the remaining docking stations 100B–100D act as slaves. Docking stations 100 are electrically coupled together via bus input connectors 166A–166D (collectively referred to as bus input connectors 166), first bus output connectors 156A–156D (collectively referred to as first bus output connectors 156) and second bus output connectors 158A–158D (collectively referred to as second bus output connectors 158). Bus connectors 156, 158 and 166 are preferably positioned on the back and both sides of a docking station 100, allowing the docking stations to be connected side-to-side or back-to-back.

Figure 6:
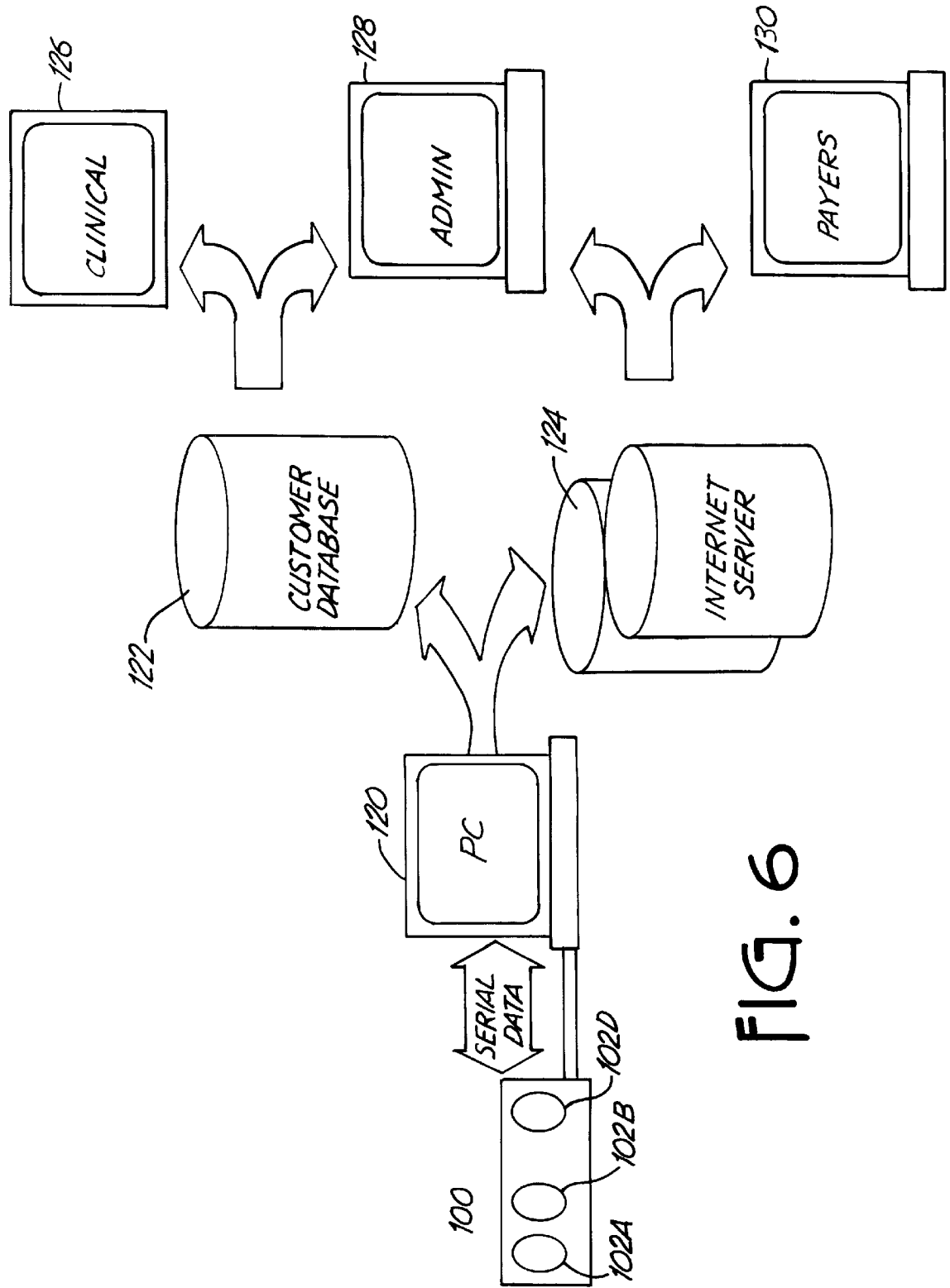
FIG. 6 is a high level flow diagram illustrating the flow of information in the present invention.

In a preferred embodiment, docking station 100 is connected to a personal computer (PC) 120 as shown in FIG. 6. After blood pressure and heart rate data are obtained by a blood pressure measurement device 10, the nurse places device 10 into a docking station 100, and PC 120 transmits commands through docking station 100 to device 10 via external connector 30. In response, device 10 outputs stored data through docking station 100 to PC 120. Concurrently, the rechargeable battery 36 within device 10 is recharged, and power is supplied to device 10 from docking station 100 via external connector 30, while device 10 is in docking station 100.

Device 10 outputs pulse rate data and blood pressure data to PC 120, including systolic blood pressure and diastolic blood pressure. Each set of pulse rate and blood pressure data includes a patient ID number, and a time stamp and a date stamp of the reading. As described above, the patient ID number is a number from 1–16 that is set using patient identification toggle 18, and allows blood pressure and pulse rate data to be organized within device 10 with respect to particular patients. In a preferred embodiment, a sensor serial number is also output from device 10 to PC 120, so that blood pressure and pulse rate information can be organized with respect to particular measurement devices 10. Device 10 may also transmit to PC 120 any other information stored in the device 10, including mean blood pressure information, usage history information and sensor test information.

PC 120 preferably includes database 122 for all of the patients in the hospital. PC 120 runs a custom software application that associates actual patients with patient ID numbers and serial numbers for devices 10. Each time PC 120 obtains information from a device 10 stored in docking station 100, PC 120 stores the information in database 122. The information obtained from devices 10 may also be stored on an Internet server 124. The information obtained from devices 10 and stored in database 122 or Internet server 124 may be accessed by other computers, such as computers 126 used by clinical personnel, computers 128 used by administrative personnel and computers 130 used by payers.

The information obtained from devices 10 through docking station 100 may be used in multiple ways. The information can be used by doctors and nurses for remote patient monitoring. The information can be used for billing purposes. Charts and graphs can be generated from the information, such as blood pressure or pulse rate historical data for a patient. The information can be used for sensor management (e.g., displaying sensor usage information, sensor test information and warnings, sensor expiration information and warnings, etc.).

Figure 7A:
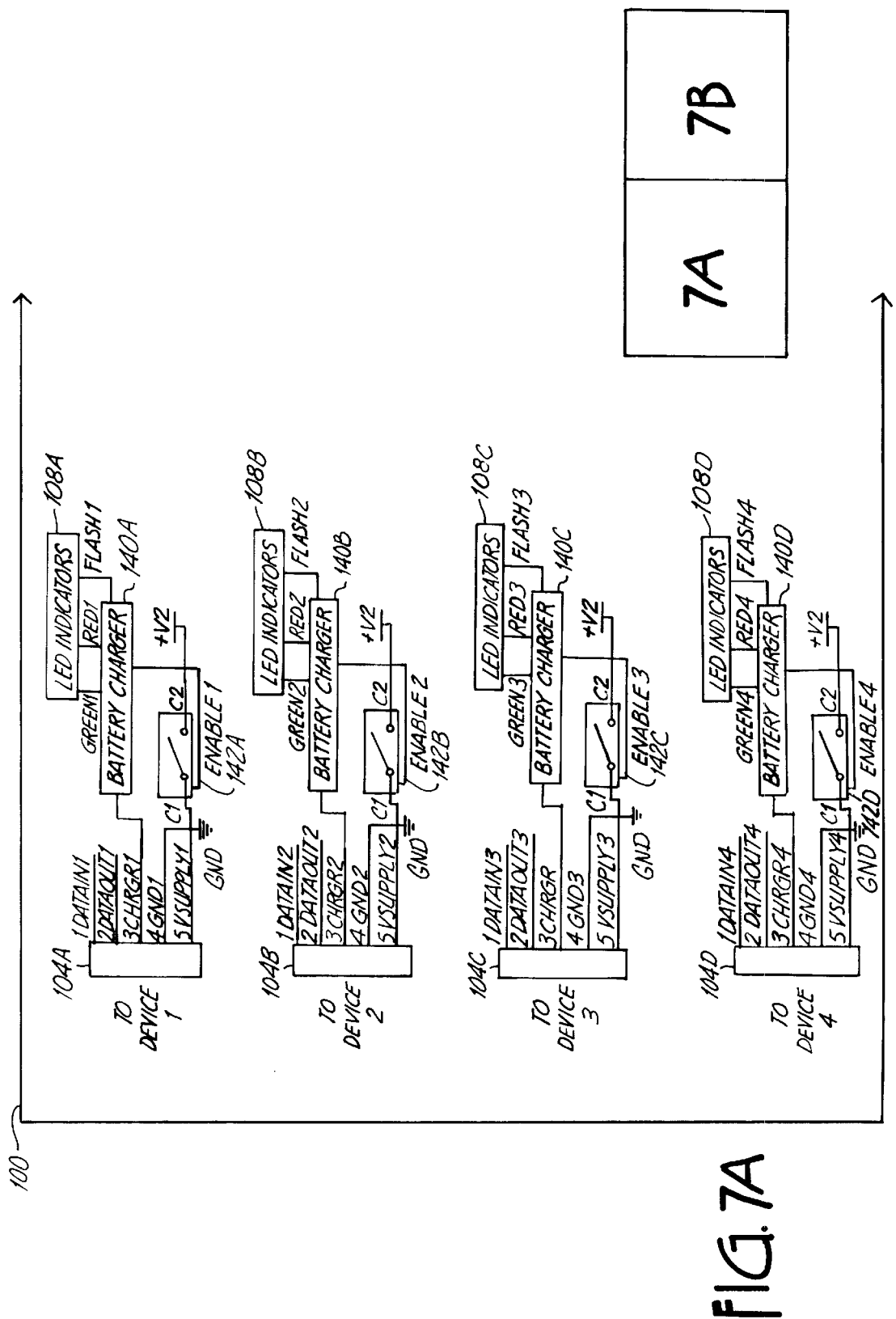
FIGS. 7A and 7B are electrical schematic diagrams of the docking station.
Figure 7B:
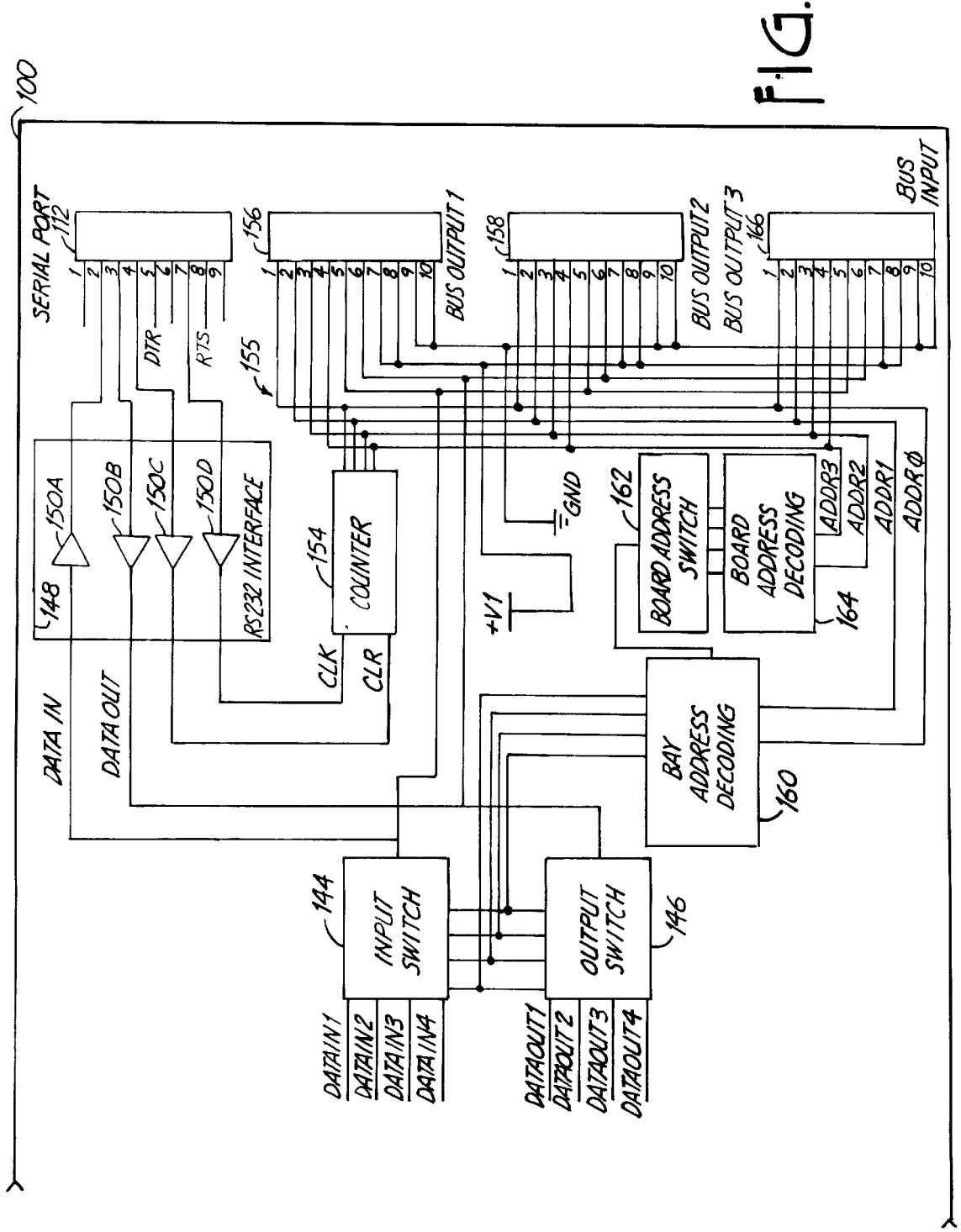

FIGS. 7A and 7B show an electrical schematic diagram of docking station 100. Docking station 100 includes five-pin connectors 104A–104D (collectively referred to as connectors 104), LED indicators 108A–108D (collectively referred to as LED indicators 108), battery chargers 140A–140D (collectively referred to as battery chargers 140), switches 142A–142D (collectively referred to as switches 142), input switch 144, output switch 146, serial interface 148, DB-9 connector 112, counter 154, first bus output 156, second bus output 158, bay address decoder 160, board address switch 162, board address decoder 164, bus input 166 and DC power supplies +V1 and +V2. Power supplies +V1 and +V2 are provided power from DC connector 110 (shown in FIG. 4).

Each connector 104 of docking station 100 may be connected to external connector 30 of a blood pressure measurement device 10. Five lines are connected to each connector 104—DATAIN, DATAOUT, CHRGR, GND and VSUPPLY. Each DATAIN line connects with the TX line of a device 10 (see FIG. 3), and is used for transmitting data from device 10 to docking station 100. The DATAIN line from each connector 104 is connected to input switch 144. Each DATAOUT line connects with the RX line of a device 10, and is used for transmitting data from docking station 100 to a device 10. The DATAOUT line from each connector 104 is connected to output switch 146. Each GND line within docking station 100 is connected to the GND line of a device 10, and is coupled to ground.

Each CHRGR line of docking station 100 connects with the CHRGR line of a device 10. Each CHRGR line of docking station 100 is also coupled to one of the battery chargers 140. Battery chargers 140 provide a current source for recharging battery 36 within a device 10. Battery chargers 140A–140D are coupled to LED indicators 108A–108D, respectively. When a device 10 is first plugged into a bay 102 of docking station 100, for example bay 102A, battery charger 140A detects the presence of device 10, begins charging device 10, starts a timer, and uses the RED1 output line to cause LED indicator 108A to display a red light. The display of the red light indicates that device 10 is charging. In a preferred embodiment, battery charger 140A monitors the timer and uses the GREEN1 and FLASH1 output lines to cause LED indicator 108A to display a flashing green light after 15 hours of charging. If device 10 is removed from bay 102A, and then replaced back in bay 102A, battery charger 140A resets the timer. Other battery chargers with different charging times may be used. Battery chargers 140B–140D operate in the same manner as battery charger 140A.

Each VSUPPLY line of docking station 100 is connected to the VSUPPLY line of a device 10, and is used to provide power to device 10. Each VSUPPLY line of docking station 100 is connected to one of the switches 142. Each switch 142 is controlled by one of the battery chargers 140. When a device 10 is first plugged into a bay 102 of docking station 100, for example bay 102A, battery charger 140A detects the presence of the device 10, and closes switch 142A. Power is then supplied to the device 10 from power supply +V2. Supplying power to device 10 from power supply +V2 guarantees not only that the digital voltage levels are the same in device 10 and docking station 100 (optimizing noise margin and reducing likelihood of latch-up and/or damage), but that the saved pressure readings, pulse rates and other data in device 10 may be obtained even with a fully discharged battery 36.

When multiple docking stations 100 are coupled together as shown in FIG. 5, one docking station 100A is a master unit, and the remaining docking stations 100B–100D are slave units. The slave units 100B–100D are similar to the master unit 100A, with the deletion of counter 154, serial interface 148 and DB-9 connector 112. When multiple docking stations 100 are connected together, only the master docking station 100A connects directly to PC 120, while the remaining docking stations 100 share a common bus 155 for communicating with PC 120.

Each docking station 100 includes a first bus output 156, a second bus output 158 and a bus input 166, which are each implemented with a 10-pin connector. Each bus line coupled to first bus output 156 is also coupled to a corresponding pin of second bus output 158 and bus input 166. The bus lines are numbered from 1 to 10. Bus lines 1–4 are connected to lines ADDR0, ADDR1, ADDR2 and ADDR3, respectively. Bus line 5 is connected to input switch 144. Bus line 6 is connected to output switch 146. Bus lines 7 and 8 are connected to +V1, which is a DC power supply. Bus lines 9 and 10 are connected to ground.

In a preferred embodiment, bus input connector 166 is positioned on the left side of docking station 100, first bus output connector 156 is positioned on the back side of docking station 100, and second bus output connector 158 is positioned on the right side of docking station 100. Other configurations are possible.

Each docking station 100 includes a circuit board for holding and connecting the electronics in FIGS. 7A and 7B. When multiple docking stations 100 are coupled together, each circuit board (and correspondingly each docking station 100) is assigned a board address. The board address for each docking station 100 is set with board address switch 162. Similarly, each bay 102 within a docking station 100 is assigned a bay address. Each circuit board and each bay 102 is assigned one address in the set {00, 01, 10, 11}. The lines ADDR0 and ADDR1 are used to cycle through the four bay addresses. The lines ADDR2 and ADDR3 are used to cycle through the four board addresses.

DB-9 connector 112 of docking station 100 is preferably connected to a serial port of PC 120, although DB-9 connector 112 may alternatively be connected to any other device that is able to manipulate TX, RX, DTR (Data Terminal Ready), and RTS (Request to Send) lines. In order to access bays 102, and therefore the blood pressure measurement devices 10, PC 120 toggles the RTS line, which then toggles the CLK line of counter 154. Counter 154 generates binary addresses in a sequence of 0 (i.e., 0000) to 15 (i.e., 1111). The first two digits of the four digit binary address represent a board address and are sent out on lines ADDR2 and ADDR3. The last two digits of the four digit binary address represent a bay address and are sent out on lines ADDR0 and ADDR1. The DTR line may toggled by PC 120 in order to reset counter 154 to 0. In this way, the data may be re-synchronized at any time to start from board 00, bay 00.

When counter 154 toggles to a new address, the new address goes out to bay address decoder 160 and board address decoder 164. Board address decoder 164 includes four output lines, each output line corresponding to one of the four possible board addresses. Board address decoder 164 decodes the two digit board address portion of the four digit address and, based on the decoded address, sets one of its four output lines high. If the line set high by board address decoder 164 corresponds to the board address set at board address switch 162, board address switch 162 sends an enable signal to bay address decoder 160, allowing bay address decoder 160 to decode the bay address. If the line set high by board address decoder 164 does not correspond to the board address set at board address switch 162, board address switch 162 maintains its output line low, thereby maintaining bay address decoder 160 in a disabled state.

Bay address decoder 160 includes four output lines, each output line corresponding to one of the four possible bay addresses. When bay address decoder 160 is enabled by board address switch 162 and receives a bay address, bay address decoder 160 decodes the bay address and, based on the decoded address, sets one of its four output lines high. The output lines of bay address decoder 160 are coupled to input switch 144 and output switch 146. Based on the output of bay address decoder 160, input switch 144 and output switch 146 couple the DATAIN and DATAOUT lines for the currently selected bay 102 to serial interface 148 and to bus lines 5 and 6. Serial interface 148 includes amplifiers 150A–150D, which amplify signals on the DATAIN, DATAOUT, DTR/CLR and RTS/CLK lines.

After toggling to a new address, PC 120 sends characters on the DATAOUT line and then waits for a response. If PC 120 does not receive a response within an allotted time, PC 120 assumes that no blood pressure measurement device 10 is present at the current board and bay address, moves on to the next board and bay address, and repeats the process. If a blood pressure measurement device 10 is present at the current board and bay address, the device 10 responds by sending characters to PC 120 on the DATAIN line. In this fashion, PC 120 is constantly scanning bays 102, looking for blood pressure measurement devices 10 that may be present.

Although the present invention has been described with reference to preferred embodiments, workers skilled in the art will recognize that changes may be made in form and detail without departing from the spirit and scope of the invention.

What is claimed is:

1. A storage device for storing a plurality of portable medical devices, each portable medical device including an electrical connector, the storage device comprising:
   a plurality of bays for receiving and storing the plurality of portable medical devices, each bay including a first electrical connector, the first electrical connector of each bay configured to interface with the electrical connector of one of the portable medical devices;
   a second electrical connector configured to be coupled to a computer;
   a battery charger coupled to at least one of the first electrical connectors of a bay for charging a battery of one of the portable medical devices; and
   switch means coupled to the first electrical connector of each bay and coupled to the second electrical connector for selectively coupling each bay to the computer for data transfer between the portable medical devices and the computer.

2. The storage device of claim 1, and further comprising means for supplying power to a portable medical device when the device is placed in one of the plurality of bays.

3. The storage device of claim 1, wherein the plurality of portable medical devices are non-invasive blood pressure measurement devices.

4. The storage device of claim 1, and further comprising a plurality of indicator lights, each indicator light positioned adjacent one of the bays, each indicator light indicating a charging status of one of the portable medical devices.

5. The storage device of claim 4, wherein each indicator light is a dualcolor LED.

6. The storage device of claim 1, and further comprising at least one third electrical connector configured to be connected to a second storage device for storing a plurality of portable medical devices.

7. The storage device of claim 1, and further comprising at least three bus connectors, each bus connector configured to be connected to a storage device for storing a plurality of portable medical devices.

8. The storage device of claim 1, wherein the storage device comprises a master unit and at least one slave unit, the master unit and the slave unit each including a plurality of bays for receiving and storing the plurality of portable medical devices, the master unit and the slave unit each including a bus connector for electrically coupling the master unit to the slave unit.

9. The storage device of claim 8, wherein the master unit and the slave unit each include multiple bus connectors to connect the master unit and the slave unit together in multiple alternative configurations.

10. A method of gathering and centrally storing a set of patient data for each of a plurality of patients, the method comprising:
    applying a plurality of non-invasive blood pressure measurement devices to a plurality of patients to obtain the patient data;
    storing the patient data in the plurality of non-invasive blood pressure measurement devices;
    placing the plurality of non-invasive blood pressure measurement devices in a docking station coupled to a computer; and
    transmitting the stored data from each non-invasive blood pressure measurement device through the docking station to the computer and storing the patient data therein.

11. The method of claim 10, and further comprising storing a patient identifier in each set of patient data.

12. The method of claim 11, and further comprising storing a time and a date stamp in each set of patient data, the time and the date stamp indicating the time and the date that the set of patient data was obtained.

13. The method of claim 11, and further comprising storing a device identifier in each non-invasive blood pressure measurement device and transmitting the device identifier from each non-invasive blood pressure measurement device through the docking station to the computer.

14. The method of claim 10, and further comprising storing device usage history information in each non-invasive blood pressure measurement device, and transmitting the device usage history information from each non-invasive blood pressure measurement device through the docking station to the computer.

15. The method of claim 10, and further comprising storing device test information in each non-invasive blood pressure measurement device, and transmitting the device test information from each non-invasive blood pressure measurement device through the docking station to the computer.

16. The method of claim 10, and further comprising generating and displaying patient status information based on the patient data stored in the computer.

17. The method of claim 10, and further comprising generating billing information based on patient data stored in the computer.

18. The method of claim 10, wherein the portable medical devices are non-invasive blood pressure measurement devices.

19. The method of claim 10, wherein the patient data includes systolic and diastolic blood pressure information.

20. The method of claim 10, and further comprising supplying power to at least one of the non-invasive blood pressure measurement devices when the device is placed in the docking station.

21. The method of claim 10, and further comprising recharging a battery of at least one of the non-invasive blood pressure measurement devices when the device is placed in the docking station.

* * * * *

UNITED STATES PATENT AND TRADEMARK OFFICE
CERTIFICATE OF CORRECTION

PATENT NO. : 6,524,240 B1  Page 1 of 1
DATED : February 25, 2003
INVENTOR(S) : Roger C. Thede It is certified that error appears in the above-identified patent and that said Letters Patent is hereby corrected as shown below:

<u>Column 12,</u>
Lines 26-28, please delete claim 18 in its entirety.
Line 29, claim reference number "19" should read -- 18 --
Line 31, claim reference number "20" should read -- 19 --
Line 35, claim reference number "21" should read -- 20 --.

Signed and Sealed this

Thirteenth Day of April, 2004

JON W. DUDAS
*Acting Director of the United States Patent and Trademark Office*